(12) United States Patent
Baril et al.

(10) Patent No.: US 11,071,559 B2
(45) Date of Patent: Jul. 27, 2021

(54) TISSUE SPECIMEN RETRIEVAL DEVICES WITH INTEGRATED BAG CUT-OFF MECHANISM

(71) Applicant: COVIDIEN LP, Mansfield, MA (US)

(72) Inventors: Jacob C. Baril, Norwalk, CT (US); Saumya Banerjee, Hamden, CT (US)

(73) Assignee: Covidien LP, Mansfield, MA (US)

(*) Notice: Subject to any disclaimer, the term of this patent is extended or adjusted under 35 U.S.C. 154(b) by 174 days.

(21) Appl. No.: 16/546,565

(22) Filed: Aug. 21, 2019

(65) Prior Publication Data
US 2021/0052291 A1    Feb. 25, 2021

(51) Int. Cl.
*A61B 17/00* (2006.01)
*A61B 17/221* (2006.01)
*A61B 17/22* (2006.01)

(52) U.S. Cl.
CPC ...... *A61B 17/221* (2013.01); *A61B 17/00234* (2013.01); *A61B 17/22031* (2013.01); *A61B 2017/00287* (2013.01); *A61B 2017/2212* (2013.01); *A61B 2017/2215* (2013.01)

(58) Field of Classification Search
CPC .......... A61B 17/221; A61B 2017/2212; A61B 2017/2215; A61B 17/22031; A61B 2017/00287; A61B 17/00234
See application file for complete search history.

(56) References Cited

U.S. PATENT DOCUMENTS

| | | |
|---|---|---|
| 5,578,048 A | 11/1996 | Pasqualucci et al. |
| 5,647,372 A | 7/1997 | Tovey et al. |
| 8,734,464 B2 | 5/2014 | Grover et al. |
| 8,777,961 B2 | 7/2014 | Cabrera et al. |
| 8,968,329 B2 | 3/2015 | Cabrera |
| 9,549,747 B2 | 1/2017 | Carlson |
| 9,592,067 B2 | 3/2017 | Hartoumbekis |
| 9,987,031 B2 | 6/2018 | Menn |
| 9,993,229 B2 | 6/2018 | Whitfield |
| 10,034,661 B2 | 7/2018 | Holsten et al. |
| 10,154,833 B2 | 12/2018 | Holsten et al. |
| 2019/0321018 A1 | 10/2019 | Prior |

*Primary Examiner* — Wade Miles
(74) *Attorney, Agent, or Firm* — Carter, DeLuca & Farrell LLP

(57) ABSTRACT

A tissue specimen retrieval device includes a first shaft and a second shaft telescopically movable relative to the first shaft. The second shaft supports an end effector assembly at a distal end portion thereof and is movable relative to the first shaft between a retracted position, wherein the end effector assembly is disposed within the first shaft, and a deployed position, wherein the end effector assembly extends distally from the first shaft. The end effector assembly includes a tissue specimen bag supported by a first arm and a second arm. The first and second arms are configured to open the tissue specimen bag when the second shaft is deployed. A cut-off slider is operably associated with the distal end portion of the second shaft and is configured to sever the tissue specimen bag upon retraction of the second shaft.

20 Claims, 4 Drawing Sheets

TISSUE SPECIMEN RETRIEVAL DEVICES WITH INTEGRATED BAG CUT-OFF MECHANISM

BACKGROUND

Technical Field

The present disclosure relates to tissue specimen retrieval from an internal body cavity and, more particularly, to tissue specimen retrieval devices to facilitate retrieval of a tissue specimen from an internal body cavity.

Background of Related Art

In minimally-invasive surgical procedures, operations are carried out within an internal body cavity through small entrance openings in the body. The entrance openings may be natural passageways of the body or may be surgically created, for example, by making a small incision into which an access device is inserted.

Minimally-invasive surgical procedures may be used for partial or total retrieval of a tissue specimen from an internal body cavity. However, the restricted access provided by minimally-invasive openings (natural passageways and/or surgically created openings) presents challenges with respect to maneuverability and visualization. The restricted access also presents challenges when the tissue specimen is required to be removed. As such, a tissue specimen that is deemed too large for intact retrieval may be broken down into a plurality of smaller pieces to facilitate retrieval from the internal body cavity.

During such minimally-invasive surgical procedures, it is common that a cyst, tumor, or other affected tissue specimen is required to be removed. In these and other procedures where cancerous tissue is required to be removed, retrieval of the tissue specimen in an enclosed environment is highly desirable to inhibit seeding of cancer cells. Thus, with respect to breaking down large tissue specimens for retrieval through minimally-invasive openings, there is the added challenge of doing so within an enclosed environment.

SUMMARY

In accordance with the present disclosure is a tissue specimen retrieval device that includes a first shaft and a second shaft telescopically movable relative to the first shaft. The second shaft supports an end effector assembly at a distal end portion thereof and is movable relative to the first shaft between a retracted position, wherein the end effector assembly is disposed within the first shaft, and a deployed position, wherein the end effector assembly extends distally from the first shaft. The end effector assembly includes a tissue specimen bag supported by a first arm and a second arm. The first and second arms are configured to open the tissue specimen bag when the second shaft is deployed. A cut-off slider is operably associated with the distal end portion of the second shaft and is configured to sever the tissue specimen bag upon retraction of the second shaft.

In aspects according to the present disclosure, the cut-off slider includes a blade disposed therein. In other aspects according to the present disclosure, the cut-off slider includes a pair of first and second opposing flanges configured to ride atop respective first and second arms during movement of the tissue specimen bag to the deployed position, the first or second flange including a blade disposed therein configured to cut the tissue specimen bag upon retraction of the second shaft.

In aspects according to the present disclosure, one or both of the flanges includes a detent(s) at a proximal end thereof configured to operably engage a corresponding slot(s) defined within a distal portion of the first shaft upon deployment of the tissue specimen bag. In other aspects according to the present disclosure, the detent(s) engages the corresponding slot(s) upon complete deployment of the tissue specimen bag. In still other aspects according to the present disclosure, each flange includes a detent at a proximal end thereof configured to engage a corresponding slot defined within the distal portion of the first shaft. In yet other aspects according to the present disclosure, the detents are outwardly biased to facilitate engagement within respective slots defined within the first shaft.

In aspects according to the present disclosure, the cut-off slider is prevented from retracting proximally when the second shaft is retracted thereby enabling the cut-off slider to sever the tissue specimen bag upon retraction of the second shaft. In other aspects according to the present disclosure, the detent(s) locks within the slot(s) preventing the cut-off slider from retracting proximally when the second shaft is retracted thereby enabling the blade to sever the tissue specimen bag upon retraction of the second shaft.

In aspects according to the present disclosure, the blade is spaced relative to a distal end of the first flange. In yet other aspects according to the present disclosure, when the detents engage the corresponding slots, the pair of first and second opposing flanges remains spaced relative to the distal portion of the first shaft to ensure that the entire tissue specimen bag is not severed upon retraction of the second shaft.

In aspects according to the present disclosure, the cut-off slider is generally I-beam shaped and includes a pair of first and second opposing flanges separated by an interconnecting web, the pair of first and second flanges are configured to ride atop corresponding first and second arms upon deployment of the tissue specimen bag.

In accordance with aspects of the present disclosure, a tissue specimen retrieval device includes a first shaft and a second shaft telescopically movable relative to the first shaft. The second shaft is configured to support an end effector assembly at a distal end portion thereof and is movable relative to the first shaft between a retracted position, wherein the end effector assembly is disposed within the first shaft, and a deployed position, wherein the end effector assembly extends distally from the first shaft. The end effector assembly includes a tissue specimen bag supported by a first arm and a second arm configured to open the tissue specimen bag when the second shaft is deployed. A cut-off slider is operably associated with the distal end portion of the second shaft. The cut-off slider is generally I-shaped and includes a pair of first and second opposing flanges separated by an interconnecting web. The pair of first and second opposing flanges is configured to ride atop respective first and second arms. The cut-off slider includes a blade recessed within one or both of the first and second opposing flanges. The blade is configured to sever the tissue specimen bag upon retraction of the second shaft.

In aspects according to the present disclosure, one or both of the flanges includes a detent at a proximal end thereof, the detent is configured to operably engage one or more corresponding slots defined within a distal portion of the first shaft upon deployment of the tissue specimen bag. In aspects according to the present disclosure, the detent(s) engages the corresponding slot(s) upon complete deployment of the tissue specimen bag.

In aspects according to the present disclosure, each flange includes a detent at a proximal end thereof configured to engage a corresponding slot defined within the distal portion of the first shaft. In other aspects according to the present disclosure, the detents are outwardly biased to facilitate engagement within respective slots defined within the first shaft.

In aspects according to the present disclosure, the cut-off slider is prevented from retracting proximally when the second shaft is retracted thereby enabling the blade to sever the tissue specimen bag upon retraction of the second shaft. In other aspects according to the present disclosure, the detent(s) locks within the slot(s) preventing the cut-off slider from retracting proximally when the second shaft is retracted thereby enabling the blade to sever the tissue specimen bag upon retraction of the second shaft.

In aspects according to the present disclosure, the blade is spaced relative to a distal end of the first flange. In yet other aspects according to the present disclosure, when the detents engage the corresponding slots, the pair of first and second opposing flanges remains spaced relative to the distal portion of the first shaft to ensure that the entire tissue specimen bag is not severed upon retraction of the second shaft.

BRIEF DESCRIPTION OF THE DRAWINGS

The accompanying drawings, which are incorporated in and constitute a part of this specification, illustrate embodiments of the present disclosure and, together with the detailed description below, serve to further explain the present disclosure, in which.

DETAILED DESCRIPTION

Figure 1:
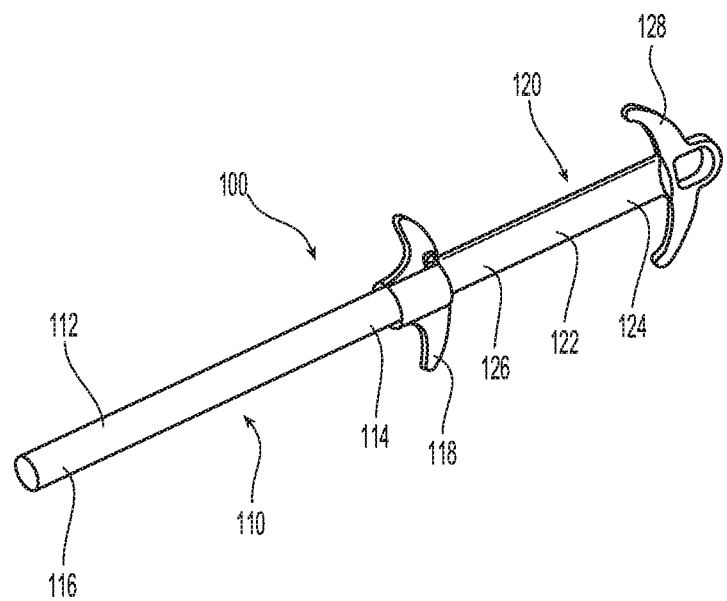
FIG. 1 is a perspective view of a tissue specimen retrieval device provided in accordance with aspects of the present disclosure, disposed in a retracted position.

As used herein, the term "distal" refers to the portion that is being described which is further from a user, while the term "proximal" refers to the portion that is being described which is closer to a user. Further, to the extent consistent, any of the aspects and features detailed herein may be used in conjunction with any or all of the other aspects and features detailed herein.

As used herein, the terms parallel and perpendicular are understood to include relative configurations that are substantially parallel and substantially perpendicular up to about + or −10 degrees from true parallel and true perpendicular.

"About" or "approximately" as used herein may be inclusive of the stated value and means within an acceptable range of variation for the particular value as determined by one of ordinary skill in the art, considering the measurement in question and the error associated with measurement of the particular quantity (e.g., the limitations of the measurement system). For example, "about" may mean within one or more standard variations, or within ±30%, 20%, 10%, 5% of the stated value.

Descriptions of technical features or aspects of an exemplary embodiment of the present disclosure should typically be considered as available and applicable to other similar features or aspects in another exemplary embodiment of the present disclosure. Accordingly, technical features described herein according to one exemplary embodiment of the present disclosure may be applicable to other exemplary embodiments of the present disclosure, and thus duplicative descriptions may be omitted herein.

Exemplary embodiments of the present disclosure will be described more fully below (e.g., with reference to the accompanying drawings). Like reference numerals may refer to like elements throughout the specification and drawings.

Figure 2:
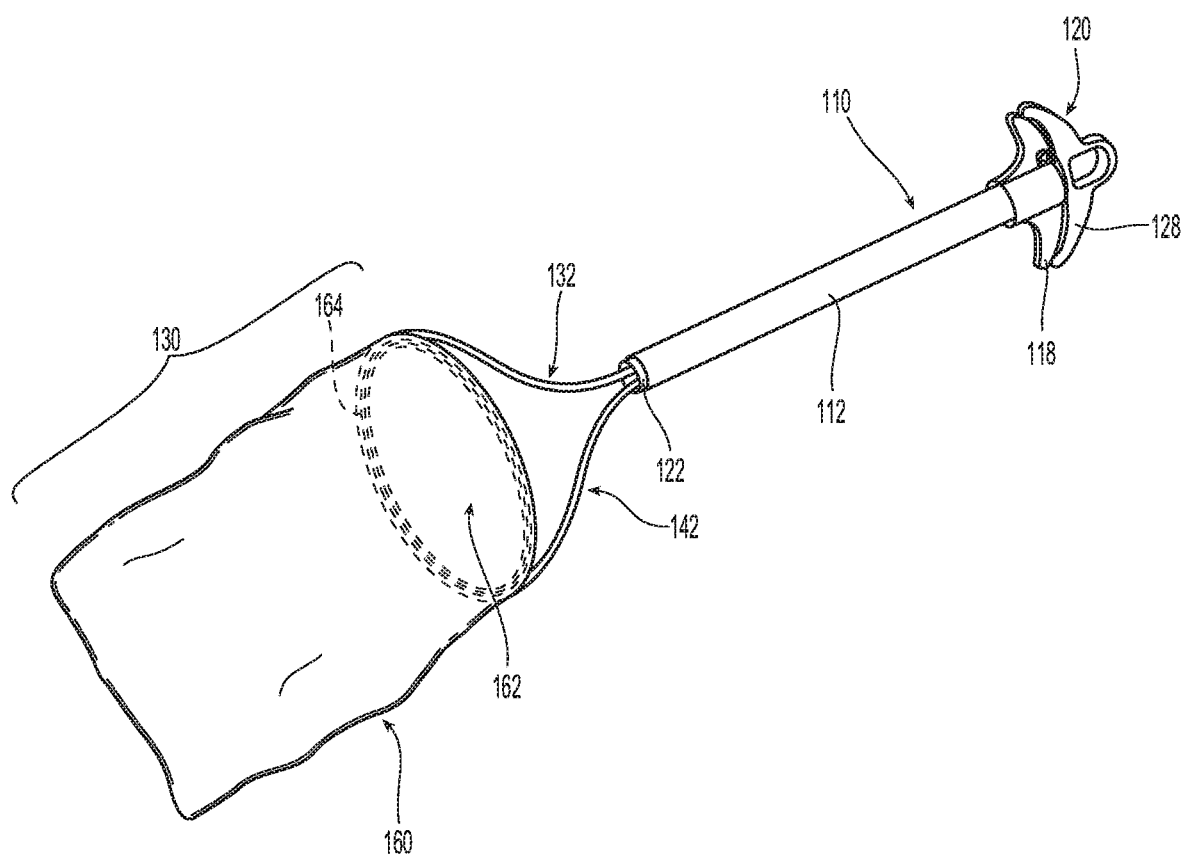
FIG. 2 is a perspective view of the tissue specimen retrieval device of FIG. 1, disposed with the arms of an end effector assembly fully deployed for retrieving tissue specimens.

Referring to FIGS. 1-2, a tissue specimen retrieval device provided in accordance with the present disclosure is shown generally identified by reference numeral 100. Tissue specimen retrieval device 100 includes a first body 110, a second body 120, and an end effector assembly 130 including a specimen bag 160. First body 110 includes a first shaft 112 defining a proximal end portion 114 and a distal end portion 116. First body 110 further includes a first handle 118 disposed at proximal end portion 114 of first shaft 112. First handle 118 may be engaged with proximal end portion 114 of first shaft 112, monolithically formed with proximal end portion 114 of first shaft 112, or otherwise secured thereto in any suitable manner that enables a user to grasp and manipulate first handle 118 to thereby control manipulation of first shaft 112.

Second body 120 includes a second shaft 122 defining a proximal end portion 124 and a distal end portion 126. Second shaft 122 supports end effector assembly 130 at distal end portion 126 of second shaft 122 and is telescopically slidably within and relative to first shaft 112 between a retracted position of tissue specimen retrieval device 100 (FIG. 1), wherein end effector assembly 130 is disposed within first shaft 112, and a deployed position of tissue specimen retrieval device 100 (FIG. 2), wherein end effector assembly 130 extends distally from first shaft 112. Second body 120 further includes a second handle 128 disposed at proximal end portion 124 of second shaft 122. Second handle 128 may be engaged with proximal end portion 124 of second shaft 122, monolithically formed with proximal end portion 124 of second shaft 122, or otherwise secured thereto in any suitable manner that enables a user to grasp and manipulate second handle 128 to thereby control manipulation of second shaft 122. Second handle 128, more specifically, is movable relative to first handle 118 from a spaced-apart position (FIG. 1) to an approximated position (FIG. 2) to move tissue specimen retrieval device 100 from the retracted position (FIG. 1), wherein end effector assembly 130 is disposed within first shaft 112, to the deployed position (FIG. 2), wherein end effector assembly 130 extends distally from first shaft 112.

Figure 3:
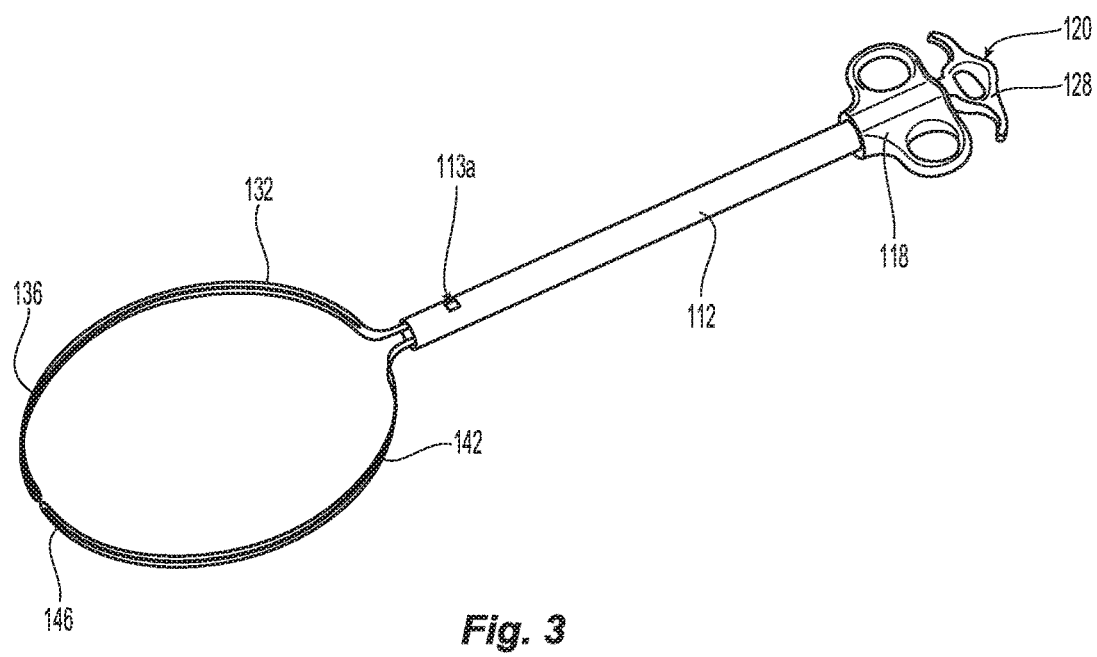
FIG. 3 is a perspective view of an end effector assembly of the tissue specimen retrieval device of FIG. 2 with the specimen bag removed therefrom.

Referring to FIGS. 2 and 3, end effector assembly 130, as noted above, is supported at distal end portion 126 of second shaft 122. End effector assembly 130, more specifically, includes first and second arms 132, 142 extending distally from distal end portion 126 of second shaft 122 and a specimen bag 160 supported by and depending from first and second arms 132, 134. Each of first and second arms 132, 142 includes a proximal segment 133, 143 engaged with and extending distally from distal end portion 126 of second shaft 122, and a distal portion 136, 146 extending distally from respective proximal segments 133, 143.

Arms 132, 142 are substantially co-planar with one another and are formed from resiliently flexible material, e.g., nitinol, that biases arms 132, 142 towards an expanded position. Arms 132, 142 each define, in the first expanded position, a curvature along at least a portion of the length thereof such that the two arms define a generally circular configuration for supporting bag 160. One or both arms 132, 142 may include a fenestration disposed therealong to facilitate transition between the expanded position and a collapsed or retracted position.

Arms 132, 142 are resiliently flexible between the expanded position and the collapsed position, wherein the curvatures of arms 132, 142 are at least partially eliminated and the distal portions 136, 146 are moved closer to one another, e.g., such that proximal segments 134, 144 are moved towards a substantially parallel orientation. Proximal segments 133, 143 are configured to resiliently flex within the plane defined thereby such that proximal segments 133, 143 remain substantially co-planar with one another in each of and during movement between the expanded and collapsed positions.

With reference to FIG. 2, distal portions 136, 146 support specimen bag 160 thereon with specimen bag 160 depending therefrom. Specimen bag 160 may be formed from any suitable bio-compatible material (or materials), e.g., ripstop nylon, configured to retain a tissue specimen therein. Specimen bag 160 defines at least one opening, e.g., open end 162 thereof, for receipt of a tissue specimen therein. Specimen bag 160 may include one or more channels 164 formed about at least a portion of the perimeter of open end 162 thereof for retaining arms 132, 142 therein to support specimen bag 160.

Turning back to FIGS. 1-3, in the retracted position of tissue specimen retrieval device 100 (FIG. 1), as noted above, end effector assembly 130 is disposed within first shaft 112 of first body 110. Once deployed, the end effector 130 transitions to the expanded position and the specimen bag 160 can be oriented to receive a tissue specimen. Once the tissue specimen is received, the second shaft 122 is pulled proximally to collapse the arms 132, 142 and the bag 160 within the first shaft 112.

Figure 4:
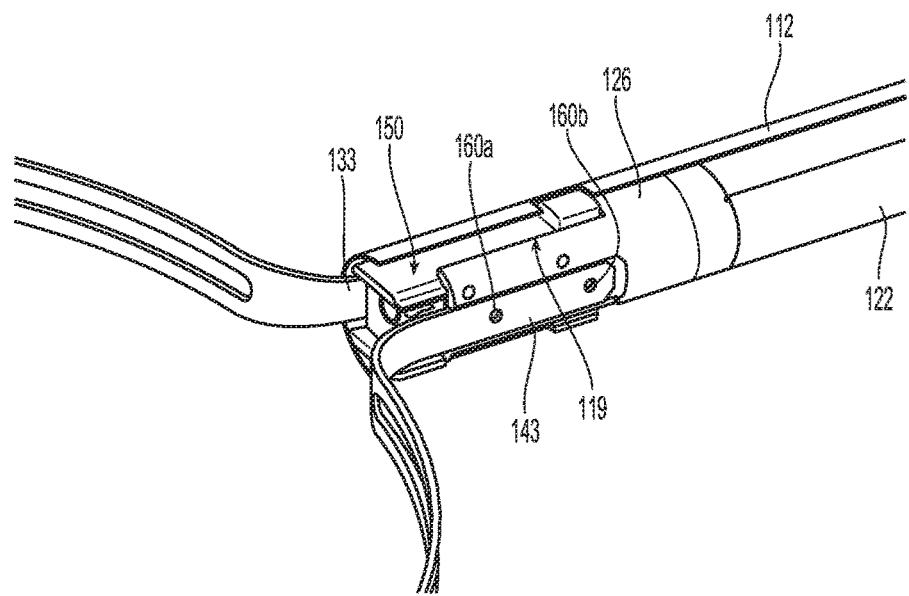
FIG. 4 is an enlarged, partial internal, perspective view of the end effector assembly of the tissue specimen retrieval device of FIG. 1 in a fully deployed position and illustrating the cut-off mechanism in a deployed position.
Figure 5A:
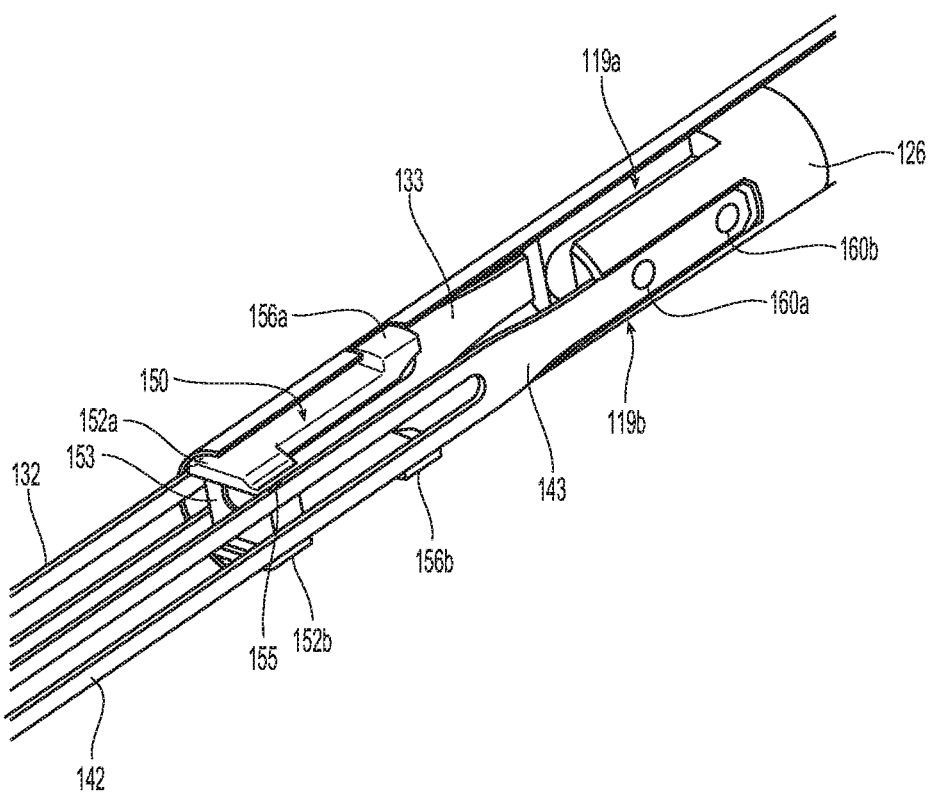
FIG. 5A is an enlarged, internal, perspective view of the end effector assembly of the tissue specimen retrieval device of FIG. 1 illustrating the bag arms being retracted with the cut-off mechanism in a deployed position and positioned to cut the tissue specimen bag as the bag arms retract.
Figure 5B:
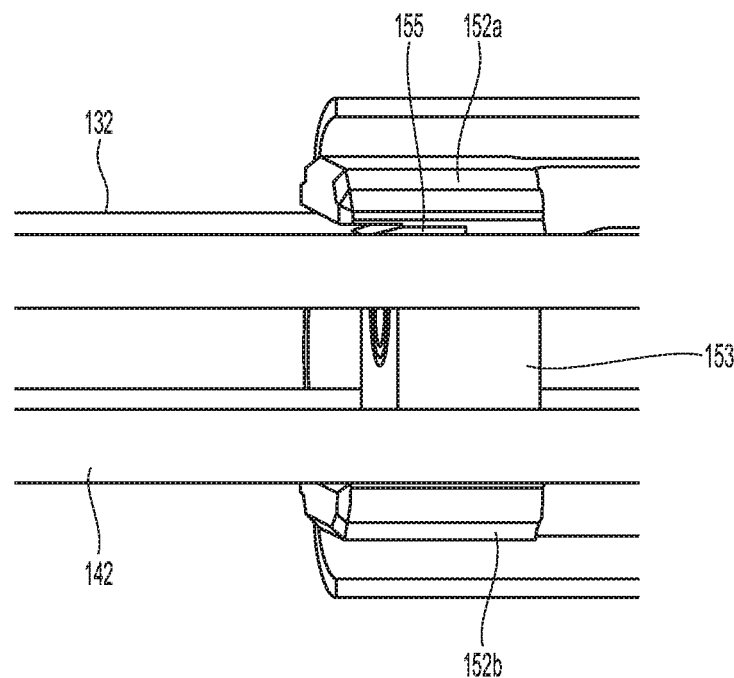
FIG. 5B is a greatly-enlarged view of a distal end of the cut-off mechanism.
Figure 5C:
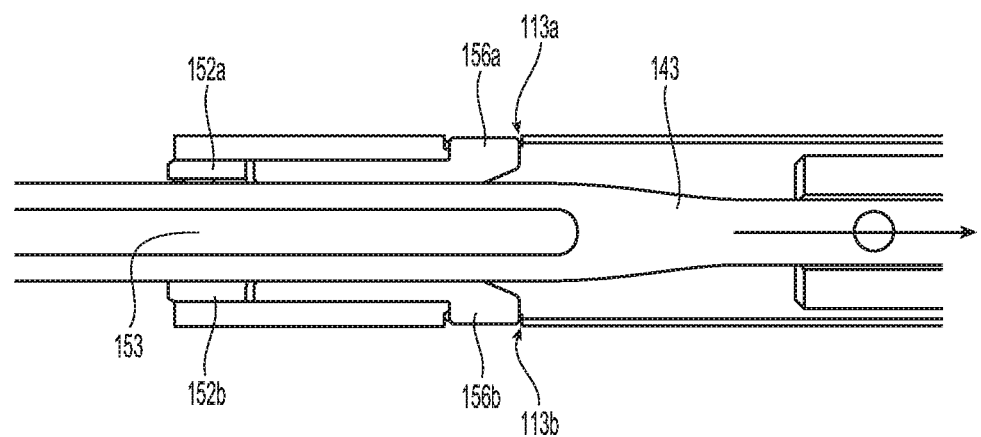
FIG. 5C is an internal, side view showing movement of the bag arms relative to a fixed cutting mechanism during retraction of the tissue specimen retrieval device.

FIGS. 4, 5B and 5C show internal views of the distal ends 116, 126 of respective shafts 112 and 122 and the various mechanical connections and internal components thereof. More particularly, proximal portion 143 of arm 142 is mechanically engaged to detents 160a, 160b disposed on the distal portion 126 of shaft 122 (mechanical connections are not shown with respect to arm 132 but are similar). A cut-off slider 150 is disposed at a distal end of shaft 122 and is removably retained in a pair of slots 119a, 119b defined in the distal portion 126 thereof. Cut-off slider 150 is generally I-beam shaped and includes a pair of opposing flanges 152a, 152b separated by an interconnecting web 153.

Flanges 152a, 152b are configured to slide atop each arm 132, 142 during deployment and retraction of the bag 160. More particularly, flange 152a is configured to transverse the area defined between top surfaces of arms 132, 142 and ride therealong during deployment and retraction and flange 152b is configured to transverse the area defined between bottom surfaces of arms 132, 142 and ride therealong during deployment and retraction. Web 153 is configured to provide stability between the two flanges 152a, 152b during sliding. A blade 155 is recessed within flange 152a and is configured to cut the tissue specimen bag 160 during retraction of the arms 132, 142 within shaft 112 as explained in more detail below. The blade 155 is recessed for safety purposes. Flange 152b may also contain a blade (not shown) depending upon a particular purpose.

Each flange 152a, 152b of cut-off slider 150 also includes a proximal detent 156a, 156b that is cantilevered or outwardly biased with respect to flanges 152a, 152b, respectively. More particularly, each proximal detent 156a, 156b is configured to flex relative to the each respective flange 152a, 152b when the cut-off slider 150 transitions from a proximal orientation, i.e., when shaft 122 is retracted within shaft 112, and move distally with arms 132, 142 to deploy the specimen bag 160. When disposed in the proximal orientation, the proximal detents 156a, 156b are nested within opposing slots or cavities 119a, 119b defined in the distal end 126 of shaft 122 (See FIG. 5A). As the bag 160 deploys, the proximal detents 156a, 156b initially ride along with the arms 132, 142 within shaft 112.

When the cut-off slider 150 reaches the distal-most end of shaft 112, the detents 156a, 156b lock into respective opposing slots 113a, 113b of shaft 112 preventing further movement of the cut-off slider 150 relative to shafts 112 and 122. The arms 132, 142 are free to fully deploy the bag 160 while the flanges 152a, 152b remain stationary. The arms 132, 142 simply ride under the flanges 152a, 152b to complete deployment of the bag 160. The cut-off slider 150 remains locked within opposing slots 113a, 113b during specimen retrieval and retraction of the bag 160 and arms 132, 142 as explained in more detail below.

After specimen collection, the surgeon retracts shaft 122 relative to shaft 112 pulling arms 132, 142 proximally within the shaft 112. Detents 160a, 160b disposed on the distal portion 126 of shaft 122 maintain the proximal end 133, 143 of arms 132, 142 secured to the distal portion 126 during retraction. Upon retraction, the arms 132, 142 slide under the flanges 152a, 152b as the arms 132, 142 are received within the distal end 116 of shaft 112. As the arms 132, 142 slide proximally under flange 152a, the recessed blade 155 disposed in flange 152a cuts a top portion of bag 160 allowing the bag 160 to slide off of arms 132, 142. The surgeon holds the specimen and the bag 160 as the bag 160 is being cut.

In embodiments, shaft 112 or 122 may include one or more mechanisms to dislodge the detents 156a, 156b from opposing slots 113a, 113b to reset the specimen retrieval device 100 if desired. In this instance, another bag may be reloaded if needed.

In embodiments, the opposite flange 152b or both flanges 152a, 152 may include a blade 155 to cut the bag 160 during retraction. The blade 155 may also be set back or spaced a short distance from a distal end of the flange 152a to ensure that the bag 160 is not entirely severed from the arms 132, 142 during retraction. As can be appreciated, this would ensure that the bag 160 does not fall from the device unexpectedly when the shaft 122 is being retracted.

The various embodiments disclosed herein may also be configured to work with robotic surgical systems and what is commonly referred to as "Telesurgery." Such systems employ various robotic elements to assist the surgeon and allow remote operation (or partial remote operation) of surgical instrumentation. Various robotic arms, gears, cams, pulleys, electric and mechanical motors, etc. may be employed for this purpose and may be designed with a robotic surgical system to assist the surgeon during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of surgeons or nurses may prep the patient for surgery and configure the robotic surgical system with one or more of the instruments disclosed herein while another surgeon (or group of surgeons) remotely control the instruments via the robotic surgical system. As can be appreciated, a highly skilled surgeon may perform multiple operations in multiple locations without leaving his/her remote console which can be both economically advantageous and a benefit to the patient or a series of patients.

The robotic arms of the surgical system are typically coupled to a pair of master handles by a controller. The handles can be moved by the surgeon to produce a corresponding movement of the working ends of any type of surgical instrument (e.g., end effectors, graspers, knifes, scissors, etc.) which may complement the use of one or more of the embodiments described herein. The movement of the master handles may be scaled so that the working ends have a corresponding movement that is different, smaller or larger, than the movement performed by the operating hands of the surgeon. The scale factor or gearing ratio may be adjustable so that the operator can control the resolution of the working ends of the surgical instrument(s).

The master handles may include various sensors to provide feedback to the surgeon relating to various tissue parameters or conditions, e.g., tissue resistance due to manipulation, cutting or otherwise treating, pressure by the instrument onto the tissue, tissue temperature, tissue impedance, etc. As can be appreciated, such sensors provide the surgeon with enhanced tactile feedback simulating actual operating conditions. The master handles may also include a variety of different actuators for delicate tissue manipulation or treatment further enhancing the surgeon's ability to mimic actual operating conditions.

From the foregoing and with reference to the various figure drawings, those skilled in the art will appreciate that certain modifications can also be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A tissue specimen retrieval device, comprising:
   a first shaft;
   a second shaft telescopically movable relative to the first shaft, the second shaft supporting an end effector assembly at a distal end portion thereof and movable relative to the first shaft between a retracted position, wherein the end effector assembly is disposed within the first shaft, and a deployed position, wherein the end effector assembly extends distally from the first shaft, the end effector assembly including a tissue specimen bag supported by a first arm and a second arm, the first and second arms configured to open the tissue specimen bag when the second shaft is in the deployed position; and
   a cut-off slider operably associated with the distal end portion of the second shaft, the cut-off slider configured to sever the tissue specimen bag upon retraction of the second shaft.

2. The tissue specimen retrieval device of claim 1, wherein the cut-off slider includes a blade disposed therein.

3. The tissue specimen retrieval device of claim 1, wherein the cut-off slider includes a pair of first and second opposing flanges configured to ride atop respective first and second arms during movement of the tissue specimen bag to the deployed position, at least the first flange including a blade disposed therein configured to cut the tissue specimen bag upon retraction of the second shaft.

4. The tissue specimen retrieval device of claim 3, wherein at least one of the flanges includes a detent at a proximal end thereof, the at least one detent configured to operably engage at least one corresponding slot defined within a distal portion of the first shaft upon deployment of the tissue specimen bag.

5. The tissue specimen retrieval device of claim 4, wherein the at least one detent engages the at least one corresponding slot upon complete deployment of the tissue specimen bag.

6. The tissue specimen retrieval device of claim 4, wherein the at least one detent locks within the at least one slot preventing the cut-off slider from retracting proximally when the second shaft is retracted thereby enabling the blade to sever the tissue specimen bag upon retraction of the second shaft.

7. The tissue specimen retrieval device of claim 4, wherein when the at least one detent engages the at least one corresponding slot , the pair of first and second opposing flanges remains spaced relative to the distal portion of the first shaft to ensure that the entire tissue specimen bag is not severed upon retraction of the second shaft.

8. The tissue specimen retrieval device of claim 3, wherein each flange includes a detent at a proximal end thereof configured to engage a corresponding slot defined within the distal portion of the first shaft.

9. The tissue specimen retrieval device of claim 8, wherein the detents are outwardly biased to facilitate engagement within respective slots defined within the first shaft.

10. The tissue specimen retrieval device of claim 1, wherein the cut-off slider is prevented from retracting proximally when the second shaft is retracted thereby enabling the cut-off slider to sever the tissue specimen bag upon retraction of the second shaft.

11. The tissue specimen retrieval device of claim 3, wherein the blade is spaced relative to a distal end of the first flange.

12. The tissue specimen retrieval device of claim 1, wherein the cut-off slider is generally I-beam shaped and includes a pair of first and second opposing flanges separated by an interconnecting web, the pair of first and second flanges configured to ride atop corresponding first and second arms upon deployment of the tissue specimen bag.

13. A tissue specimen retrieval device, comprising:
   a first shaft;

a second shaft telescopically movable relative to the first shaft, the second shaft supporting an end effector assembly at a distal end portion thereof and movable relative to the first shaft between a retracted position, wherein the end effector assembly is disposed within the first shaft, and a deployed position, wherein the end effector assembly extends distally from the first shaft, the end effector assembly including a tissue specimen bag supported by a first arm and a second arm, the first and second arms configured to open the tissue specimen bag when the second shaft is in the deployed position; and a cut-off slider operably associated with the distal end portion of the second shaft, the cut-off slider generally I-shaped and including a pair of first and second opposing flanges separated by an interconnecting web, the pair of first and second opposing flanges configured to ride atop respective first and second arms, the cut-off slider including a blade recessed within at least one of the first and second opposing flanges, the blade configured to sever the tissue specimen bag upon retraction of the second shaft.

14. The tissue specimen retrieval device of claim 13, wherein at least one of the flanges includes a detent at a proximal end thereof, the at least one detent configured to operably engage at least one corresponding slot defined within a distal portion of the first shaft upon deployment of the tissue specimen bag.

15. The tissue specimen retrieval device of claim 14, wherein the at least one detent engages the at least one corresponding slot upon complete deployment of the tissue specimen bag.

16. The tissue specimen retrieval device of claim 14, wherein the at least one detent locks within the at least one slot preventing the cut-off slider from retracting proximally when the second shaft is retracted thereby enabling the blade to sever the tissue specimen bag upon retraction of the second shaft.

17. The tissue specimen retrieval device of claim 14, wherein when the at least one detent engages the at least one corresponding slot , the pair of first and second opposing flanges remains spaced relative to the distal portion of the first shaft to ensure that the entire tissue specimen bag is not severed upon retraction of the second shaft.

18. The tissue specimen retrieval device of claim 13, wherein each flange includes a detent at a proximal end thereof configured to engage a corresponding slot defined within the distal portion of the first shaft.

19. The tissue specimen retrieval device of claim 18, wherein the detents are outwardly biased to facilitate engagement within respective slots defined within the first shaft.

20. The tissue specimen retrieval device of claim 13, wherein the cut-off slider is prevented from retracting proximally when the second shaft is retracted thereby enabling the blade to sever the tissue specimen bag upon retraction of the second shaft.

* * * * *